(12) United States Patent
Verbeeck et al.

(10) Patent No.: US 9,153,412 B2
(45) Date of Patent: Oct. 6, 2015

(54) GENERATION OF CHARGED PARTICLE VORTEX WAVES

(71) Applicant: UNIVERSITEIT ANTWERPEN, Antwerp (BE)

(72) Inventors: Johan Verbeeck, Hever (BE); Gustaaf Van Tendeloo, Kessel (BE)

(73) Assignee: UNIVERSITEIT ANTWERPEN, Antwerp (BE)

( * ) Notice: Subject to any disclaimer, the term of this patent is extended or adjusted under 35 U.S.C. 154(b) by 0 days.

(21) Appl. No.: 14/367,487

(22) PCT Filed: Dec. 19, 2012

(86) PCT No.: PCT/EP2012/076234
§ 371 (c)(1),
(2) Date: Jun. 20, 2014

(87) PCT Pub. No.: WO2013/092764
PCT Pub. Date: Jun. 27, 2013

(65) Prior Publication Data
US 2014/0346354 A1 Nov. 27, 2014

(30) Foreign Application Priority Data
Dec. 20, 2011 (GB) .................................. 1121879.9

(51) Int. Cl.
*H01J 37/10* (2006.01)
*H01J 37/04* (2006.01)
*H01J 37/26* (2006.01)
*G01N 23/225* (2006.01)

(52) U.S. Cl.
CPC ............ *H01J 37/04* (2013.01); *G01N 23/2251* (2013.01); *H01J 37/26* (2013.01);
(Continued)

(58) Field of Classification Search
CPC ................. H01J 37/32009; H01J 3/02; H01J 2203/0296; H01J 2237/06383; H01J 2237/2614; H01J 2237/24557; H01J 37/06; H01J 2237/2802; H01J 23/087; H01J 2237/055; H01J 27/18; G21K 1/16; G21K 1/003
USPC .......................................... 250/251, 307, 311
See application file for complete search history.

(56) References Cited

U.S. PATENT DOCUMENTS 4,175,830 A * 11/1979 Marie ....................... 359/484.01
9,018,596 B2 * 4/2015 Verbeeck et al. .......... 250/396 R
(Continued)

OTHER PUBLICATIONS

Uchida, Masaya et al., "Generation of Electron Beams Carrying Orbital Angular Momentum", Nature, Macmillan Publishers Limited, vol. 464, No. 7289, Apr. 1, 2010, pp. 737-739.
(Continued)

*Primary Examiner* — Brooke Purinton
(74) *Attorney, Agent, or Firm* — Workman Nydegger

(57) ABSTRACT

A device is arranged for imparting an orbital angular momentum to a charged particle wave propagating along an axis in a charged particle beam generating apparatus. The device includes a first conductive element comprising a plurality of angularly spaced electrical conductors arranged around the axis, and a second conductive element. The first and second conductive elements are spaced apart along the direction of the axis, and are adapted for transmitting a charged particle wave propagating along the axis. A connecting means is adapted for supplying an electrical potential to the plurality of angularly spaced electrical conductors for inducing an angular gradient of the phase of the charged particle wave when transmitted along the axis, in which the projection along the axis of the electrical potential varies as a function of an angular position with respect to the axis.

15 Claims, 5 Drawing Sheets

(52) U.S. Cl.
CPC ........ *H01J 37/263* (2013.01); *G01N 2223/101* (2013.01); *H01J 2237/1504* (2013.01); *H01J 2237/24557* (2013.01); *H01J 2237/24564* (2013.01); *H01J 2237/2614* (2013.01)

(56) References Cited

U.S. PATENT DOCUMENTS

| | | | |
|---|---|---|---|
| 2008/0035854 A1* | 2/2008 | Jin et al. | 250/396 R |
| 2008/0296509 A1* | 12/2008 | Schroder et al. | 250/398 |
| 2009/0039257 A1* | 2/2009 | Essers et al. | 250/307 |
| 2011/0192976 A1* | 8/2011 | Own et al. | 250/311 |

OTHER PUBLICATIONS

Verbeeck, J. et al., "Production and Application of Electron Vortex Beams", Nature, Macmillan Publishers Limited, vol. 467, No. 7313, Sep. 16, 2010, pp. 301-304.

Verbeeck, J., et al., "Atomic Scale Electron Vortices for Nanoresearch", American Institute of Physics, Applied Physics Letters, vol. 99, No. 20, Nov. 2011, pp. 203109-1-203109-3.

Barton, B. et al., "In-Focus Electron Microscopy of Frozen-Hydrated Biological Samples with a Boersch Phase Plate", Ultramicroscopy, Elsevier, vol. 111, No. 12, Sep. 12, 2011, pp. 1696-1705.

Alloyeau, D. et al, "Imaging of Soft and Hard Materials Using a Boersch Phase Plate in a Transmission Electron Microscope", Ultramicroscopy, Elsevier, vol. 110, No. 5, Apr. 1, 2010, pp. 563-570.

Verbeeck, J. et al., "A New Way of Producing Electron Vortex Probes for STEM", Ultramicroscopy, vol. 113, Oct. 29, 2011, pp. 83-87.

McMorran, B.J., et al., "Electron Vortex Beams with High Quanta of Orbital Angular Momentum", Science, vol. 331, No. 6014, Jan. 14, 2011, pp. 192-195.

Search Report from corresponding GB Application No. 1121879.9, Jul. 17, 2012.

International Search Report from corresponding International Application PCT/EP2012/076234, Mar. 13, 2013.

\* cited by examiner

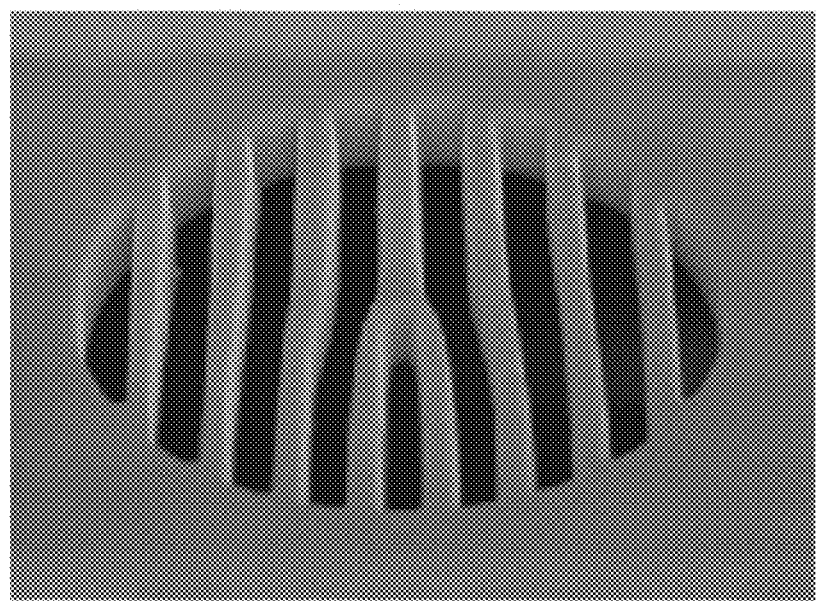
FIG. 1 – PRIOR ART
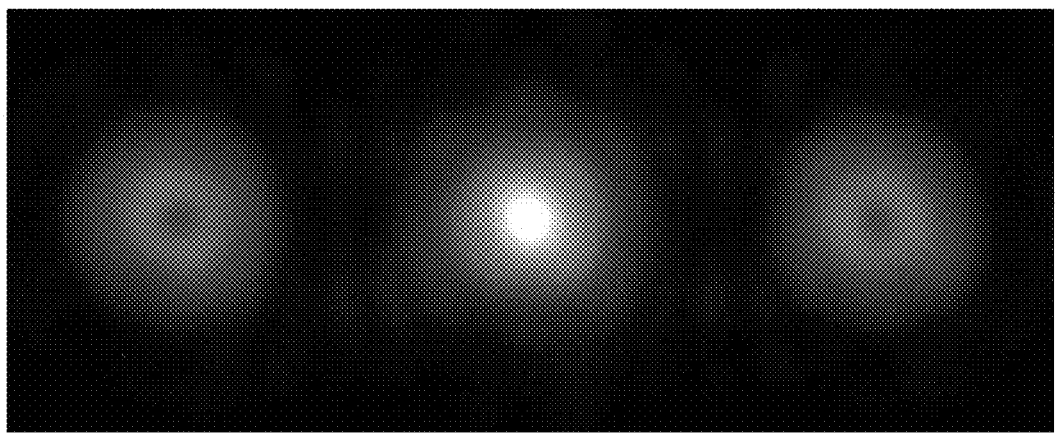
FIG. 2 – PRIOR ART

GENERATION OF CHARGED PARTICLE VORTEX WAVES

FIELD OF THE INVENTION

The invention relates to the field of charged particle beam manipulation. More specifically it relates to methods and systems for imparting an orbital angular momentum to a charged particle beam, e.g. an electron beam used in electron microscopy.

BACKGROUND OF THE INVENTION

Most wave phenomena encountered in physics textbooks consider planar or spherical waves, which both have in common that their wavefronts form separated planes in space. However, waves of different topology can theoretically exist. An interesting class of such waves are so-called vortex waves, which are also known as waves with a topological charge or waves with a phase singularity.

Vortex waves were first discovered in radio waves and later found many applications in light optics. Such waves carry an orbital angular momentum (OAM) of $m\hbar$ per primary particle, in which the topical charge m is a non-zero integer, e.g. +1 or −1. The orbital angular momentum depends on the spatial distribution of the electromagnetic field, i.e. is carried by the vorticity of the wave and distinct from the angular momentum attributable to polarization.

Vortex waves are used in applications such as quantum information, nano-manipulation and astrophysics. Vortex waves have been obtained from different types of waves, such as radio, acoustic and X-ray waves. Recently, also electron vortex beams have been produced. Electron waves are routinely used in transmission electron microscopes because of their advantageous short wavelength, e.g. of the order of picometers, for kinetic energies of a few hundred keV. This small wavelength of accelerated electrons makes them ideal candidates for creating vortex beams of atomic size. Furthermore, electrons are charged particles and therefore carry a magnetic moment of $m\mu_B$ per electron in addition to the orbital angular momentum of $m\hbar$ per electron. This connection of OAM to magnetism makes them ideal candidates to probe the magnetic state of materials they interact with. In combination with the small wavelengths that can be obtained, this may lead to atomic resolution magnetic mapping of materials.

One application of electron vortex beams may be found in the field of electron energy loss spectroscopy (EELS). EELS is a spectroscopic technique used in transmission electron microscopy to measure the energy loss of the fast electrons when scattering inelastically in a material. The energy loss spectrum contains information about the type of atoms in the material, their chemical bonding, the electronic state and their valency. An attractive feature of EELS is that it can be obtained with a spatial resolution below 1 Å. Atomic resolution EELS experiments have been performed that show atom by atom the constitution of a given material. This is particularly of interest near interfaces and defects in materials.

The available information in EELS may be expanded to include magnetic information by making use of vortex beams, because the conservation of total angular momentum may influence the dipole selection rules that govern the possible excitations in EELS. For example, for ferromagnetic Fe and Co, a spectrum can be obtained that is similar to what is commonly obtained from X ray magnetic chiral dichroism (XCMD). XMCD makes use of absorption differences in circularly polarised X rays, while EELS with vortex electron waves may create the same incoming angular momentum with an electron beam, e.g. an electron wave carrying m=1. However, electron beams have the advantage over X-rays that atomic resolution may be achievable, as is routinely demonstrated in transmission electron microscopy.

It should be noted that a technique that offers magnetic information was already available in EELS under the name of Energy Loss Magnetic Chiral Dichroism (EMCD). EMCD is based on the interference of Bragg scattered electron beams by the crystal combined with inelastic scattering. In a situation with well defined crystal orientation and thickness, a spectrum very close to XMCD could also be obtained. However, precise control over thickness and orientation limits the range of applications in which EMCD can be used. EMCD is furthermore fundamentally limited to a spatial resolution bigger than a few unit cells, e.g. 2 nm, because elastic diffraction is essential in creating the signal. The signal to noise ratio of the technique is furthermore relatively low. Vortex electron beams on the other hand may have no fundamental limit to the maximum spatial resolution, apart from the wavelength, the orientation of the crystal plays no important role because the interference is caused by the vorticity of the beam rather than by Bragg scattering and a substantially larger signal to noise ratio may be achievable.

Methods are known in the art to produce electron vortex waves which use holographic reconstruction techniques. Such methods work by illuminating a computer calculated grating structure with a planar electron reference beam to obtain a wave with a predefined phase. The grating is typically cut from a thin metal foil, e.g. a thickness of a few 100 nm of Pt, by using a focused ion beam instrument (FIB). An example of such grating is illustrated in FIG. 1, in which a fork-shaped discontinuity can be seen that may be typical for such gratings. This is an easy method to reproduce, and in principle a grating for any value of m may be produced with this method. However, this method has the disadvantage that the grating simultaneously produces three output beams, as shown by the electron intensity as obtained from such grating in the far field depicted in FIG. 2: the vortex wave of interest, the reference beam and the complex conjugate of the vortex wave of interest, i.e. a vortex wave of opposite handedness. This means that the total electron current available is distributed over the three beams. Furthermore, the grating may typically only transmit about 50% of the electrons, which further reduces the available current in the vortex beam of interest, e.g. to a maximum of ⅛ of the total current. A sufficient current may for example be important for obtaining a high signal to noise ratio. Since these three beam components are simultaneously present, it may be difficult to isolate a signal coming from the vortex beam of interest. It may be possible to overcome this disadvantage with other apertures which select only the beam of interest, but these have other disadvantages.

An alternative method known in the art to produce vortex electron beams may use a phase grating, which is similar to a phase grating for photons, but for electrons the grating substrate has to be extremely thin to produce a phase shift of $2\pi$, e.g. less than 100 nm. This means that contamination on such a grating may deteriorate its function over time as the phase will change, although this may possibly be resolved by heating or working in better vacuum conditions.

Charged particles, such as electrons, undergo a phase shift when travelling through a confined region of space with an electrostatic potential. Such methods of phase shifting are known in the art in, for example, a Boersch phase plate. Such plate typically comprises a single electrostatic lens which may shift the phase of a central part of an electron beam relative to a distal part of the beam, i.e. a part further away from the optical axis. This technique is based on producing an electrostatic 'einzellens,' which may comprise a stack of 3 metallic planes, in which the central plate may be held at a predetermined voltage potential V, while the upper and lower planes are kept at a reference ground potential GND. Furthermore, these metallic planes are typically separated by insulating layers. A central hole may further be provided, e.g. concentrically aligned around the optical axis, in order to enable electrons to pass through. Methods of manufacture of such phase plates for application in electron microscopy are known in the art, e.g. based on focused ion beam milling.

SUMMARY OF THE INVENTION

It is an object of the present invention to provide good and efficient means and methods for providing a charged particle vortex beam.

It is an advantage of embodiments of the present invention that an isolated charged particle vortex wave may be provided, e.g. that a reference wave may be transformed into a vortex wave without generating secondary waves.

It is an advantage of embodiments of the present invention that a vortex wave may be obtained having a high particle current.

It is an advantage of embodiments of the present invention that means for providing a charged particle vortex wave may be efficiently and cost-effectively manufactured.

It is an advantage of embodiments of the present invention that a device for producing charged particle vortex waves may be provided that can be easily installed in existing equipment, e.g. an electron microscope. It is a further advantage of embodiments of the present invention that such an add-on to an existing system may be produced in a cost-efficient manner while considerably improving the capabilities of the system.

It is an advantage of embodiments of the present invention that a vortex wave may be provided having an orbital angular momentum that is tunable, e.g. that may be controlled by an external signal. It is a further advantage of embodiments of the present invention that a vortex wave may be provided having an orbital angular momentum that may be altered rapidly, e.g. which allows for rapid computer-controlled switching.

The above objective is accomplished by a method and device according to the present invention.

In a first aspect, the present invention provides in a device for imparting an orbital angular momentum to a charged particle wave propagating along an axis in a charged particle beam generating apparatus. This device comprises a first conductive element, which comprises a plurality of angularly spaced electrical conductors arranged around the axis. The device further comprises a second conductive element, in which the first conductive element and the second conductive element are spaced apart along the direction of the axis, and in which the first conductive element and the second conductive element are adapted for transmitting a charged particle wave propagating along the axis. The device furthermore comprises a connecting means for supplying an electrical potential difference over the first conductive element and the second conductive element, in which the connecting means is adapted for supplying an electrical potential to the plurality of angularly spaced electrical conductors for inducing an angular gradient of the phase of the charged particle wave when transmitted along the axis. The projection along the axis of this electrical potential varies as function of an angular position with respect to the axis.

In a device according to embodiments of the present invention, the angular gradient of the phase of the charged particle wave may be substantially equal to an integer phase shift per unit angle.

In a device according to embodiments of the present invention, the connecting means may comprise a voltage terminal for receiving an externally supplied voltage, a ground terminal and a plurality of resistive elements connected in series between the voltage terminal and the ground terminal to form a voltage ladder. Each angularly spaced electrical conductor may be connected to a corresponding rung of said voltage ladder. It may be an advantage of embodiments of the present invention that efficient means may be provided for supplying an angular variation around an axis of an electrostatic potential.

In a device according to embodiments of the present invention, the first conductive element may be provided with at least a first aperture and the second conductive element may be provided with at least a second aperture. The or each first aperture and the or each second aperture may be substantially aligned along the axis in order to enable transmission of a charged particle wave propagating along the axis.

In a device according to embodiments of the present invention, the at least first aperture may comprise an aperture provided in each of the plurality of angularly spaced electrical conductors. It may be an advantage of embodiments of the present invention that local regions of substantially homogenous electrostatic potential may be provided by simple and efficient means in a potential which varies as function of angular position in relation to a central axis.

A device according to embodiments of the present invention may furthermore comprise a first electrically insulating spacer for spacing apart the first conductive element and the second conductive element. It may be an advantage of embodiments of the present invention that devices may be provided that are robust and mechanically stable.

A device according to embodiments of the present invention may furthermore comprise a third conductive element adapted for transmitting a charged particle wave propagating along the axis and arranged such that the first conductive element is spaced apart from and positioned between the second conductive element and the third conductive element along the direction of the axis. It may be an advantage of embodiments of the present invention that devices may be provided that are electrically shielded, e.g. that may efficiently divert charges which are deposited in the device by a charged particle wave.

In a device according to embodiments of the present invention, the connecting means may be adapted for providing a ground voltage to the second conductive element and/or the third conductive element.

A device according to embodiments of the present invention may furthermore comprise a second electrically insulating spacer for spacing apart the first conductive element and the third conductive element.

A device according to embodiments of the present invention, may furthermore comprise a controller for controlling the electrical potential supplied to the plurality of angularly spaced electrical conductors by the connecting means.

In a device according to embodiments of the present invention, the charged particle wave may be an electron wave.

In a second aspect, the present invention provides a method for imparting an orbital angular momentum to a charged particle wave. This method comprises the steps of obtaining a charged particle wave propagating in a beam along a beam axis and providing in this charged particle wave an electrical potential difference substantially oriented along the beam axis. This electrical potential difference varies as function of an angular position with respect to the beam axis in order to induce an angular gradient of the phase of the charged particle wave.

In a method according to embodiments of the present invention, the angular gradient may be substantially equal to an integer phase shift per unit angle.

The present invention may furthermore provide in a method for imaging an object, in which this method may comprise imparting an orbital angular momentum to a charged particle wave using a method according to embodiments of the present invention, impinging the charged particle wave on the object, obtaining detection data of the charged particle wave after interaction with the object and determining information about the object taking into account said detection data.

In a method according to embodiments of the present invention, this detection data may comprise an energy distribution as function of wavelength.

The present invention may furthermore provide in the use of a method according to embodiments of the present invention in electron microscopy.

In a third aspect, the present invention provides in an electron microscope for obtaining electron microscopy images. The electron microscope comprises an electron source for generating an electron beam and a device according to embodiments of the present invention for imparting an orbital angular momentum to the electron beam.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE DRAWINGS

FIG. 1 illustrates a prior-art grating for imparting orbital angular momentum to a planar electron wave.

FIG. 2 illustrates the far field electron density obtained from a prior art grating shown in FIG. 1.

Figure 3:
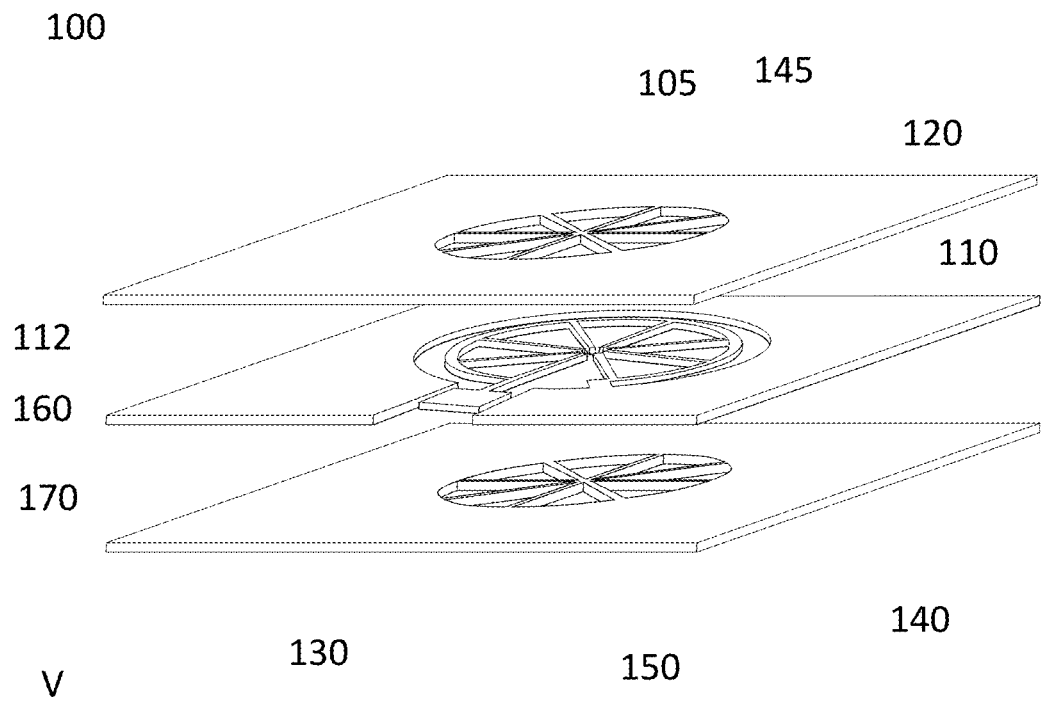
FIG. 3 shows an overview of an device according to embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to orbital angular momentum of a charged particle wave, reference is made to angular momentum carried by a charged particle wave, other than the intrinsic angular momentum of the charged particles, i.e. carried by spin polarization. Beams carrying such orbital angular momentum are also referred to as vortex waves, waves with helical wavefronts, waves having a phase singularity and waves carrying a topological charge. These charged particles may be charged elementary particles, e.g. electrons or protons, or compound particles exhibiting a conjugate particle-wave dual nature, e.g. ions. Where in the present description, for clarity sake, reference is made to electrons, it should be appreciated that embodiments of the present invention may equally well apply to other types of charged particles, such as hadrons, e.g. protons, or ions, as would be evident to a person skilled in the art. Further considerations for these other types of charged particles, e.g. relating to the specific rest mass, energy and/or charge of such particles, may be taken into account for reduction to practice, as will be readily understood by the person skilled in the art.

In a first aspect, the present invention relates to a device for imparting an orbital angular momentum to a charged particle wave propagating along an axis in a charged particle beam generating apparatus. Such charged particle wave may comprise a beam with substantially planar wavefronts, for example a planar electron beam. Particularly, the charged particle beam generating apparatus may be an electron microscope, e.g. a transmission electron microscope or a scanning electron microscope, or a focused ion beam generator. This device according to embodiments of the first aspect of the present invention comprises a first conductive element, which comprises a plurality of angularly spaced electrical conductors arranged around an axis, and a second conductive element. The first and second conductive element are spaced apart along the direction of the axis. The first and second conductive element are furthermore adapted for transmitting a charged particle wave propagating along the axis. The device also comprises a connecting means for supplying an electrical potential difference over the first and second conductive element, in which this connecting means is adapted for supplying an electrical potential to the plurality of angularly spaced electrical conductors. The projection along the axis of this electrical potential varies as function of an angular position with respect to the axis, e.g. such that an angular gradient, with respect to an angular position around the axis, of electrical potential difference between the first and the second conductive element may be supplied. Particularly, the connecting means is adapted for supplying an electrical potential to the plurality of angularly spaced electrical conductors for inducing an angular gradient of the phase of the charged particle wave when transmitted along the axis.

By way of illustration, embodiments of the present invention not being limited thereto, a number of standard and optional features will further be described with reference to FIG. 3 to FIG. 6 indicating exemplary devices or components thereof according to an embodiment of the present invention.

Figure 4:
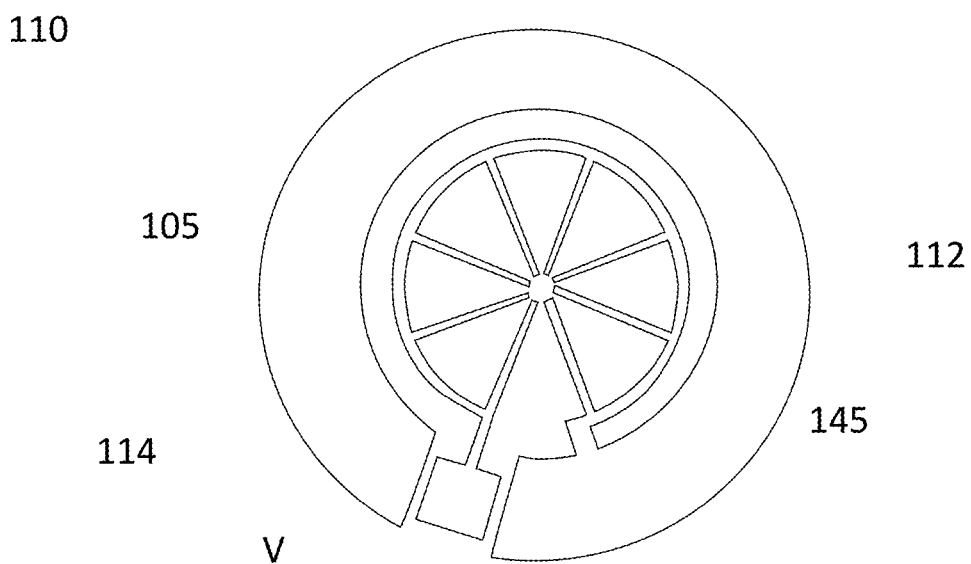
FIG. 4 shows a first conductive element according to a first embodiment of the present invention.
Figure 5:
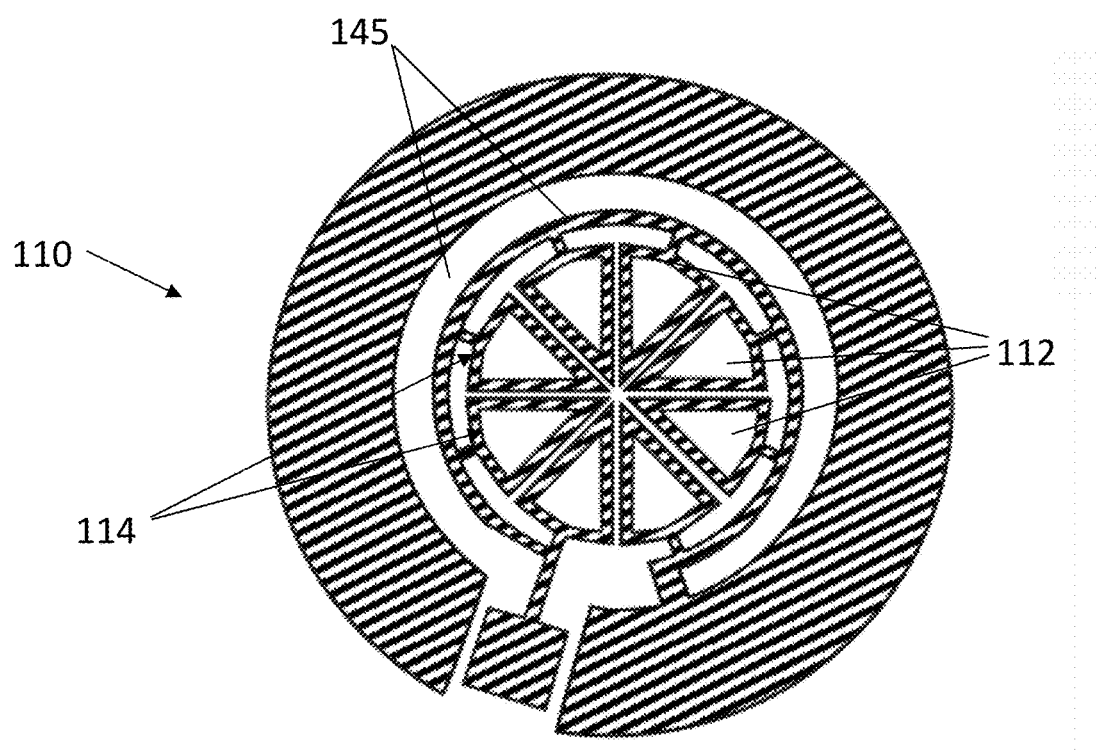
FIG. 5 shows a first conductive element according to a second embodiment of the present invention.
Figure 6:
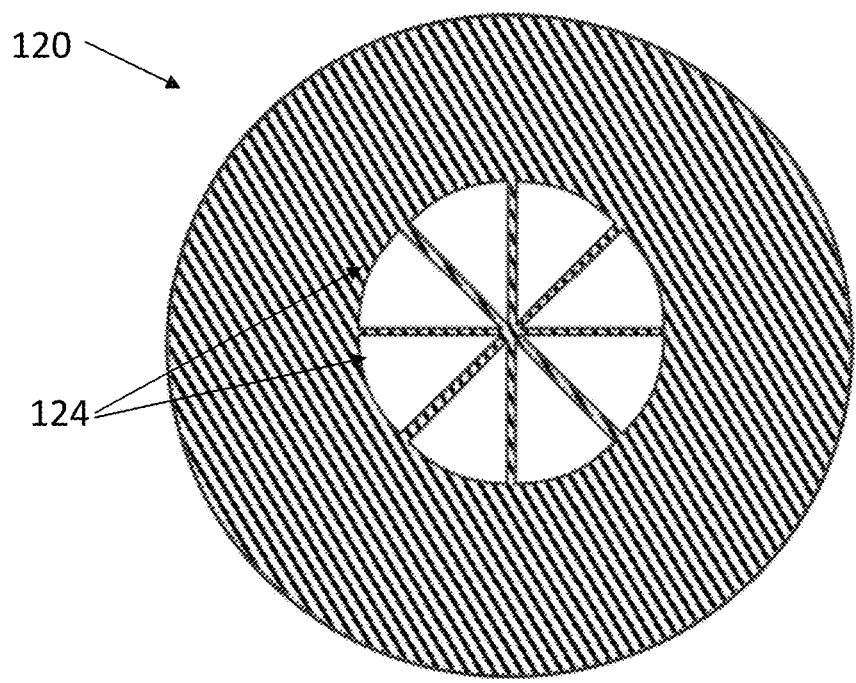
FIG. 6 shows a second conductive element according to embodiments of the present invention.

In FIG. 3, a schematic overview of a device 100 according to embodiments of this first aspect of the present invention is shown. The device 100 comprises a first conductive element 110. This first conductive element 110 comprises a plurality of angularly spaced electrical conductors 112 arranged around an axis 105, e.g. as shown in FIGS. 4 and 5. The device 100 furthermore comprises a second conductive element 120, for example as illustrated in FIG. 6. The angularly spaced electrical conductors 112 may radially extend towards the axis 105, e.g. extending from a rim structure encircling the axis 105. The angularly spaced electrical conductors 112 may act in combination with the second conductive element 120 to capacitively store an electric charge, e.g. to generate a plurality of electrostatic fields, each having a substantive component oriented in the direction of the axis 105. The number of angularly spaced electrical conductors 112 is preferably large enough to provide a sufficient sampling of a full circle, e.g. 8 conductors positioned at 45° intervals. However, as few as two angularly spaced electrical conductors 112, e.g. each covering substantially 180° around the axis 105, e.g. each forming an wedge-shaped arc of 178°, may suffice to generate a vortex wave. In embodiments having as few as two angularly spaced electrical conductors 112, astigmatism may contribute to the generation of the vortex wave. In other embodiments, more than 10 angularly spaced electrical conductors 112 may be used, for example 30 angularly spaced electrical conductors, or even 100 angularly spaced electrical conductors 112. It will be evident to the person skilled in the art that the maximum number of angularly spaced electrical conductors 112 may be merely limited by the resolution that may be achieved by the method which is used for fabrication.

While a larger number of angularly spaced electrical conductors 112 may provide a better approximation of a smooth angular gradient of the electrostatic fields generated by these electrical conductors 112 over substantially 360° around the axis 105, the electrical conductors 112 may also absorb or partially attenuate a charged particle wave directed along the axis 105. Therefore, the number of angularly spaced electrical conductors 112, e.g. 8 of such conductors, may be determined as a trade-off between charged particle wave transmission and electrostatic field smoothness.

The first and second conductive element 110,120 are spaced apart along the direction of the axis 105. When a reference voltage, e.g. a ground voltage, is applied to the second conductive element 120, and a series of increasing voltages as function of angular position in relation to the axis 105 are applied to the angularly spaced electrical conductors 112, each electrical conductor 112 may act, in cooperation with the second conductive element 120, as an electrostatic lens on a charged particle wave propagating along the axis 105, for example propagating perpendicular to the first and second conductive element 110,120. Each electrostatic lens may impart a phase shift to a local portion, e.g. a angular sector relative to the axis 105, of the charged particle wave, e.g. a shift proportional to the electrical potential difference between the second conductive element 120 and the electrical conductor 112.

The first and second conductive element 110,120 are furthermore adapted for transmitting a charged particle wave propagating along the axis 105. The first conductive element 110 may be provided with at least a first aperture 114 and the second conductive element 120 may be provided with at least a second aperture 124. The first aperture or apertures and the second aperture or apertures may be substantially aligned along the axis 105 in order to enable transmission of a charged particle wave propagating along this axis 105. For example, the first aperture 114 or apertures and the second aperture 124 or apertures may allow charged particles to pass while stopping or strongly attenuating incident charged particles outside a predetermined target region. Particularly, these apertures may provide the function of an imaging aperture in an imaging apparatus, e.g. an electron microscope.

In one embodiment, the at least one first aperture 114 may comprise a plurality of apertures, e.g. an aperture provided in each of the plurality of angularly spaced electrical conductors 112, as illustrated in FIG. 5. In such embodiment, the angularly spaced electrical conductors 112 may, for example, be substantially triangular in shape, having a corner oriented toward the axis 105. A central region of this triangular shape may have a hole provided therein such that a charged particle wave may pass through the aperture formed by such hole. An electrostatic field generated by a potential difference between such triangular conductor and the second conductive element 120 may be homogenous and substantially uniform over the opening provided by this aperture and a corresponding aperture in the second conductive element 120, e.g. in a weak-lens approximation.

In another embodiment, as illustrated in FIG. 4, the angularly spaced electrical conductors 112 may comprise elongate, rectangular conductors extending from a peripheral rim toward the axis 105. An aperture may be provided in between such elongate, rectangular conductors in order to advantageously minimize the area of the electrical conductors 112 exposed to a charged particle wave propagating along the direction of the axis 105. This may have the further advantage of allowing a simple construction, e.g. requiring few and easy to perform process steps. The electrostatic field generated by such electrical conductors 112 and the second conductive element 120 may substantially vary continuously as function of angular position relative to the axis 105, e.g. the induced phase in the charged particle wave may vary substantially linearly as function of the angular position.

The device 100 may furthermore comprise a first electrically insulating spacer 160 for spacing apart the first and second conductive elements 110,120. While electrical insulation between the first and second conductive elements 110, 120 may be merely provided by a vacuum gap, an insulating spacer 160 composed of dielectric solid material may be arranged between the first and second conductive elements 110,120, e.g. for improved robustness, electrical properties and mechanical stability. For example, the first and second conductive elements 110,120 may comprise conductive layers arranged on opposite sides of an insulator slab, e.g. a glass or silicon slab. For example, a low-stress silicon nitride membrane, e.g. composed of trisilicon tetranitride ($Si_3N_4$) or silicon dioxide ($Sio_2$), e.g. having a thickness of 100 nm, may be used as substrate material, e.g. forming the first electrically insulating spacer 160, on which gold (Au) conductive layers, e.g. having a thickness of 50 nm, are arranged. These conductive layers may be obtained by means of electron-beam lithography and electron-beam evaporation of Au. Such a membrane may be attached to a support frame, e.g. composed of 200 µm thick Si(100). Aligned apertures may be provided in the insulating spacer 160, e.g. in the silicon nitride membrane, as well as in the first and second conductive elements, e.g. gold layers, for example by means of focused ion beam lithography (FIB). The first conductive element 110 may preferably have a thickness of several 100 nm, e.g. a thickness in the range of 100 nm to 1 µm, e.g. a thickness of 200 nm, 500 nm or 800 nm, since an increased thickness of the first conductive element 110 may require a lower voltage in order to achieve an equal induced phase difference in the charged particle wave. The thickness of the second conductive element 120, and of the third conductive element 140, in embodiments in which such third conductive element 140 is provided, may be smaller than the thickness of the first conductive element 110, e.g. smaller than 100 nm, e.g. 50 nm.

In particular embodiments according to the first aspect of the present invention, the device 100 may comprise a third conductive element 140 adapted for transmitting a charged particle wave propagating along the axis 105. The third conductive element 140 may be arranged such that the first conductive element 110 is spaced apart from and positioned between the second conductive element 120 and the third conductive element 140 along the direction of the axis 105. The device 100 may furthermore comprise a second electrically insulating spacer 170 for spacing apart the first and the third conductive element 110,140, e.g. an insulating spacer 170 similar in composition and shape to the first electrically insulating spacer 160. For example, the second conductive element 120 and the third conductive element 140 may form a top and bottom layer, separated from the centrally arranged first conductive element 110 by respectively the first electrically insulating spacer 160 and the second electrically insulating spacer 170. The third conductive element 140 and the second conductive element 120 may both be connected to a common ground voltage, e.g. to provide adequate electrical shielding of the centrally arranged first conductive element 110.

The device 100 also comprises a connecting means 130 for supplying an electrical potential difference between the first conductive element 110 and the second conductive element 120. This connecting means 130 is adapted for supplying an electrical potential to the plurality of angularly spaced electrical conductors. For example, the connecting means 130 may provide a voltage to each of the angularly spaced electrical conductors 112, wherein each electrical conductor 112 receives a voltage greater than the previous electrical conductor in an angularly progressive series around the axis 105. Therefore, an angular gradient of electrical potential difference around the axis 105 may be provided. Each electrical conductor 112 may act as an electrostatic lens in combination with the second conductive element 120 for inducing an angular gradient of the phase of the charged particle wave when transmitted along the axis 105. Starting from a first electrical conductor 112, for example a grounded electrical conductor, a series of electrical conductors 112 may be traversed along a path encircling the axis 105, in which each electrical conductor 112 received a voltage higher than the previous electrical conductor 112 in this series. Alternatively, the connecting means 130 may comprise an external voltage terminal for each of the angularly spaced conductors 112, e.g. in order to enable accurate control the electrical potential on each element separately and independently.

This induced phase of the charged particle wave may be a monotonous function as function of angular position relative to the axis 105, e.g. an angle relative to a reference angular position, for example corresponding to the location of a grounded electrical conductor in the plurality of angularly spacer electrical conductors 112. For example, this monotonous function may be a strictly monotonous function, i.e. wherein each following function value for an angular position further away to 0° is higher than each previous function value for an angular position closer to 0° or wherein each following function value for an angular position further away to 0° is lower than each previous function value for an angular position closer to 0°. This angular gradient of the phase of the charged particle wave may be substantially equal to an integer phase shift per unit angle, such that a vortex wave may be generated having a predetermined topological charge, e.g. a signed topological charge representing a vorticity and a handedness of the vortex wave.

The connecting means 130 may comprise a voltage terminal for receiving an externally supplied voltage V, a ground terminal for connecting to electrical ground and a plurality of resistive elements 145 connected in series between said voltage terminal and said ground terminal to form a voltage ladder, each angularly spaced electrical conductor being connected to a corresponding rung of said voltage ladder. The connecting means 130 may furthermore be adapted for providing a ground voltage to the second conductive element and/or the third conductive element.

Furthermore, the device 100 may comprise a controller 150 for controlling this electrical potential supplied to the plurality of angularly spaced electrical conductors 112 by the connecting means, e.g. the angularly increasing electrical potential supplied by the connecting means. For example, this controller may adapt the electrical potential in order to change the topological charge of the vortex wave being generated, and/or may switch the polarity of the electrical potential in order to reverse the topological charge of this vortex wave. The controller 150 may also be adapted for controlling other parameters of the device 100, for example to control the actuation of at least one actuator (not shown), e.g. a piezoelectric element, for positioning and aligning the device 100.

The device 100 furthermore may comprise a positioning means for outlining the angularly varying electrical potential with reference to the target region. In other embodiments, the device 100 may be integrated in an aperture strip, e.g. an aperture strip for an electron microscope, such that positioning may already be provided by the aperture holder in which this aperture strip is placed.

In a second aspect, the present invention relates to a method for imparting an orbital angular momentum to a charged particle wave. This method comprises the steps of obtaining a charged particle wave propagating in a beam along a beam axis 105, and providing in this charged particle wave an electrical potential difference substantially oriented along the beam axis 105. The projection of the electrical potential difference along the beam axis 105 varies as function of an angular position with respect to the beam axis 105 in order to induce an angular gradient of the phase of the charged particle wave.

Figure 7:
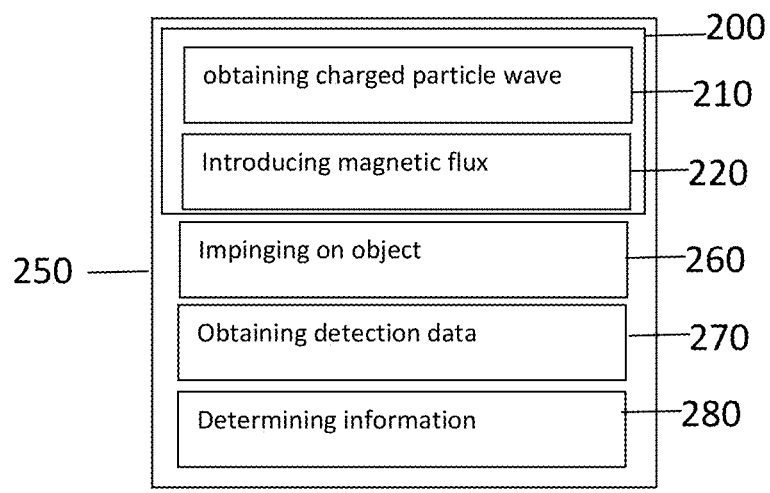
FIG. 7 shows an exemplary method according to embodiments of the present invention.

FIG. 7 shows an exemplary method 200 according to this second aspect of the present invention. This method 200 comprises obtaining 210 a charged particle wave propagating in a beam along a beam axis 105. For example such charged particle wave may be an electron wave generated in an electron microscope, such as the transmission electron microscope illustrated in FIG. 8. The method 200 furthermore comprises providing in this charged particle wave an electrical potential difference substantially oriented along the beam axis 105. For example, a device 100 according to the first aspect of the invention may be positioned into the charged particle wave in order to generate such electrical potential difference, e.g. a potential difference between the first conductive element 110 and the second conductive element 120 of the device 100. This electrical potential difference varies as function of an angular position with respect to the beam axis 105 in order to induce an angular gradient of the phase of the charged particle wave. This angular gradient of the phase may be substantially equal to an integer phase shift per unit angle, e.g. to obtain a wave of predetermined topological charge corresponding to this integer.

In a third aspect, the present invention relates to a method 250 for imaging an object. The exemplary method 250 according to embodiments of the invention, illustrated in FIG. 7, comprises imparting an orbital angular momentum to a charged particle wave using a method 200 according to the second aspect of the invention. The method 250 furthermore comprises impinging 260 the charged particle wave on the object, obtaining 270 detection data of the charged particle wave after interaction with the object and determining information 280 about the object taking into account this detection data. This detection data may comprise an energy distribution as function of wavelength.

In a fourth aspect, the present invention relates to an electron microscope 300 for obtaining electron microscopy images, the electron microscope comprising an electron source 303 for generating an electron beam and a device according to embodiments of the first aspect of the present invention for imparting an orbital angular momentum on the electron beam.

Figure 8:
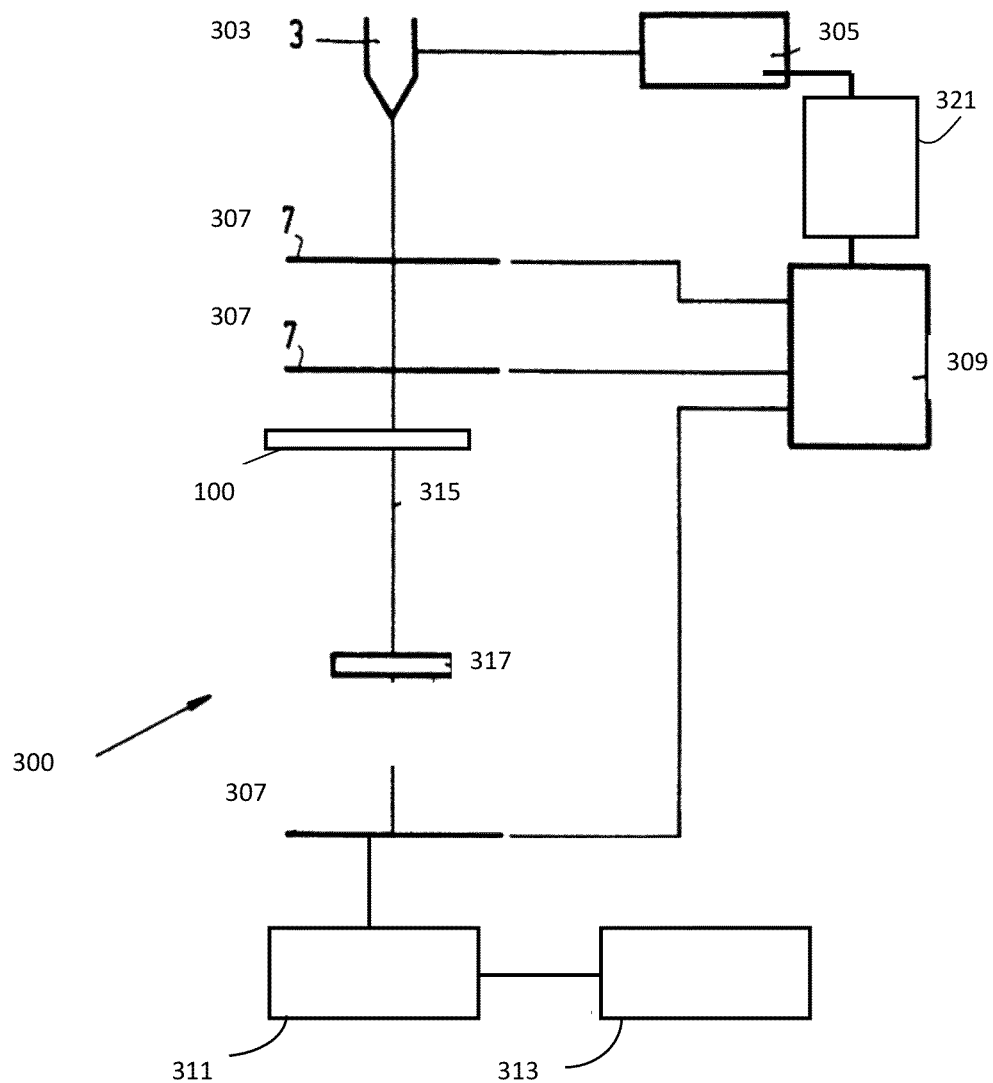
FIG. 8 is a schematic representation of a transmission electron microscope according to an embodiment of the present invention.

By way of illustration, the present invention not being limited thereto, an example of a transmission electron microscope is shown in FIG. 8. A high-resolution electron microscope 300 is shown comprising an electron source 303 which is fed by a high-voltage generator 305, and also comprises a number of lenses 307 which are fed by a lens power supply source 309. The electron microscope 301 also comprises a detection system 311, the detected information being applied to the image processing system 313. The electron beam 315 is incident on an object 317. High-resolution images of the object 317 can be recorded. The electron microscope 300 also comprises a controller 321 for controlling the imaging. Further features and advantages may be as expressed in other aspects of the present invention.

Principles of the present invention may be clarified by the description set forth hereinbelow, embodiments of the present invention not intended to be limited by such principles.

Vortex waves contain a phase change of m2π, with m an integer, when going around the vortex axis. Such vortices carry an angular momentum around the vortex axis of mℏ. For simplicity, a vortex axis parallel to the propagation axis of the running wave is assumed, but this is not a necessary condition.

The phase change Δφ that an electron wave undergoes depends on the electrostatic potential φ and the magnetic vector potential A, related to both macroscopic and microscopic fields, along its path:

$$\Delta \varphi = \frac{e}{\hbar v} \int_{path} \phi ds + \frac{e}{\hbar} \int_{path} A \cdot ds.$$

A set of electrostatic lenses may be used to produce each a different phase shift, in order to approximate a spiraling phase plate with phase shift going from 0 to m2π over a closed loop when circling around the centre of an aperture, in which m is the intended topological charge. A setup with 8 electrostatic lenses positioned in a circle around the optical axis may produce the desired effect when applying a potential to the lenses that goes stepwise from 0 V to a maximum voltage $V_{max}$ sequentially from the first to the last lens in the circle. The required potential on each lens can be reached by connecting the lenses in series and relying on the resistivity of the interconnections, e.g. by designing each connecting segment to have the same resistivity. In this way, the device may only require two external connections, i.e. connected to a ground potential GND and the maximum voltage $V_{max}$. It will be evident to the person skilled in the art, that the required potential on each lens may also be supplied by independent voltage terminals on each lens separately, e.g. to allow better external control of the setup.

The device may be adapted to be placed in a common aperture strip, e.g. specific for a type of electron microscope, with feed-through capabilities. For example, for electron microscopes, a conventional biprism aperture may be suitable.

An electrostatic vortex phase plate may increase the amount of current that is achievable in an electron vortex beam and may improve the flexibility for changing the angular momentum on the fly. The big advantage of such a setup is the fact that few electrons are lost in this process. For the conventional holographic aperture setup known in the art only 25% of all electrons that pass the holographic mask may contribute to a single vortex beam, taking into account that the holographic mask has a fill factor of 50%. This would mean approximately an 8 fold gain in electron current. Another advantage would be the flexible choice of topological charge by changing the fixed potential. A very interesting effect could occur for voltages that would create a phase plate that violates the continuity of the wavefronts, i.e. after one revolution the phase change is not an integer times $2\pi$. In principle such states are not allowed to exist but the system may force the beam properties to adapt to fulfill the requirement.

The ease with which the sign of the phase can be switched may facilitate discrimination of magnetic effects in a sample from the phase shift caused by electrostatic fields due to the presence of atoms in a crystal. This is a very important advantage because in a conventional holographic setup, the sample needs to be mechanically flipped over. This takes time and can make the method unreliable because magnetic domains can shift during this process. Therefore, embodiments of the present invention may have the advantage of providing additional information in material characterization and/or imaging by providing an efficient setup for changing the vorticity, and particularly the handedness, of a charged vortex beam. Another advantage is the strength of the phase shift. Indeed, one revolution of the spiraling current may lead to one enclosed amount of flux and an accompanying phase shift. Since the wavelength is of the order of a picometer, there may be a large number of revolutions throughout a typical transmission electron microscopy sample with a thickness of around 10 nm. The importance of this argument may be understood by the fact that currently the spatial resolution is limited by the signal to noise ratio.

Similar to optical vortex beams, trapping nanoparticles or even single atoms inside an electron vortex beam may be achievable. In optical vortex beams the trapping force is related to the energy of a dielectric medium in the inhomogeneous field of a focused beam of light, while for electrons, the interaction is more complicated due to the charge which leads to electrodynamic effects involving magnetic and electrostatic fields. The interaction depends in a complicated way on the properties of the material. The magnetic field created by the spiraling probability current of the electron vortex leads to a maximum in the magnetic field at the vortex axis. It can therefore be expected that ferromagnetic particles will get trapped inside an electron vortex beam. Inelastic interactions of the vortex electrons with the particle will transfer angular momentum and can make the particle spin. The angular velocity can quickly build up and reach the level where internal forces surpass the yield point. For a focused vortex beam, the magnetic field reaches a maximum at the focal plane and in the centre of the vortex beam. Note that the magnetic field of the microscope lenses can be eliminated making use of the so-called Lorentz lens mode. This means that potentially a levitating situation can be realised very similar to the optical trapping of single atoms. A big difference with optical trapping is however the completely different scale of the wavelength, which would allow traps of atomic dimensions possibly leading to forced interactions between particles and/or atoms. Therefore, in some aspects, the present invention also relates to the use of a method for imparting an orbital angular momentum on a charged particle beam for controlling the movement of a particle, e.g. for trapping a particle.

The invention claimed is:

1. A device for imparting an orbital angular momentum to a charged particle wave propagating along an axis in a charged particle beam generating apparatus, the device comprising a first conductive element comprising a plurality of angularly spaced electrical conductors arranged around the axis;

a second conductive element, in which said first conductive element and said second conductive element are spaced apart along the direction of said axis, and in which said first conductive element and said second conductive element are configured to transmit a charged particle wave propagating along said axis; and a voltage terminal configured to receive an externally supplied voltage, a ground terminal, and a plurality of resistive elements connected in series between said voltage terminal and said ground terminal to form a voltage ladder, wherein each angularly spaced electrical conductor is connected to a corresponding rung of said voltage ladder such that each angularly spaced electrical conductor receives a voltage greater than a previous angularly spaced electrical conductor in an angularly progressive series around said axis, wherein each angularly spaced electrical conductor acts as an electrostatic lens in combination with the second conductive element when a reference voltage is applied to the second conductive element, such as to provide an angular gradient of electrical potential difference around said axis to induce an angular gradient of the phase of the charged particle wave.

2. A device according to claim 1, in which said angular gradient of the phase of the charged particle wave is substantially equal to an integer phase shift per unit angle.

3. A device according to claim 1, in which said first conductive element is provided with at least a first aperture and said second conductive element is provided with at least a second aperture, the or each first aperture and the or each second aperture being substantially aligned along said axis in order to enable transmission of a charged particle wave propagating along said axis.

4. A device according to claim 1, in which said at least first aperture comprises an aperture provided in each of said plurality of angularly spaced electrical conductors.

5. A device according to claim 1, furthermore comprising a first electrically insulating spacer arranged for spacing apart said first conductive element and said second conductive element.

6. A device according to claim 1, furthermore comprising a third conductive element arranged for transmitting a charged particle wave propagating along said axis and arranged such that said first conductive element is spaced apart from and positioned between said second conductive element and said third conductive element along the direction of said axis.

7. A device according claim 6, furthermore comprising a second electrically insulating spacer arranged for spacing apart said first conductive element and said third conductive element.

8. A device according to claim 1, furthermore comprising a controller configured for controlling said electrical potential supplied to said plurality of angularly spaced electrical conductors by said voltage terminal, said ground terminal, and said plurality of resistive elements forming said voltage ladder.

9. A device according to claim 1, in which said charged particle wave is an electron wave.

10. An electron microscope for obtaining electron microscopy images, the electron microscope comprising an electron source for generating an electron beam and a device according to claim 1 for imparting an orbital angular momentum to said electron beam, said device according for imparting the orbital angular momentum to said electron beam including at least a first aperture provided in the first conductive element and at least a second aperture provided in the second conductive element, said apertures providing the function of an imaging aperture in said electron microscope.

11. A method for imparting an orbital angular momentum to a charged particle wave, the method comprising:
   obtaining a charged particle wave propagating in a beam along a beam axis;
   providing a first conductive element including a plurality of angularly spaced electrical conductors arranged around the beam axis;
   providing a second conductive element, in which said first conductive element and said second conductive element are spaced apart along the direction of said beam axis, and in which said first conductive element and said second conductive element are configured for transmitting the charged particle wave; and
   providing in said charged particle wave an electrical potential difference substantially oriented along said beam axis by supplying to each angularly spaced conductor a voltage greater than a voltage supplied to a previous angularly spaced electrical conductor in an angularly progressive series around said beam axis and applying a reference voltage to the second conductive element such that each angularly spaced electrical conductor acts as an electrostatic lens in combination with the second conductive element, thus providing an angular gradient of electrical potential difference around said beam axis for inducing an angular gradient of the phase of the charged particle wave.

12. A method according to claim 11, in which said angular gradient is substantially equal to an integer phase shift per unit angle.

13. A method for imaging an object, said method comprising
   imparting an orbital angular momentum to a charged particle wave using the method for imparting the orbital angular momentum to the charged particle wave according to claim 11;
   impinging said charged particle wave on the object;
   obtaining detection data of said charged particle wave after interaction with said object;
   determining information about said object taking into account said detection data; and
   providing a function of an imaging aperture in an imaging apparatus by using at least a first aperture provided in the first conductive element and at least a second aperture provided in the second conductive element.

14. A method according to claim 13, in which said detection data comprises an energy distribution as a function of wavelength.

15. A method according to claim 13 for use in electron microscopy.

* * * * *